US006808917B1

(12) United States Patent
Johnson

(10) Patent No.: US 6,808,917 B1
(45) Date of Patent: Oct. 26, 2004

(54) CONTROLLING PLANT PATHOGENS WITH FUNGAL/BACTERIAL ANATAGONIST COMBINATIONS

(76) Inventor: Thomas D. Johnson, P.O. Box 12, Buffalo, SD (US) 57720

(*) Notice: Subject to any disclaimer, the term of this patent is extended or adjusted under 35 U.S.C. 154(b) by 160 days.

(21) Appl. No.: 10/067,185

(22) Filed: Feb. 1, 2002

Related U.S. Application Data

(60) Provisional application No. 60/265,998, filed on Feb. 2, 2001.

(51) Int. Cl.[7] ................................................. C12N 1/20
(52) U.S. Cl. .............................. 435/252.4; 435/256.7; 435/252.5; 424/93.3; 424/93.46; 424/93.5; 504/117
(58) Field of Search .................... 435/252.5, 256.7, 435/252.4; 424/93.3, 93.46, 93.5; 504/117

(56) References Cited

U.S. PATENT DOCUMENTS

| | | |
|---|---|---|
| 4,476,881 A | 10/1984 | Gravely et al. |
| 4,489,161 A | 12/1984 | Papavizas |
| 4,642,131 A | 2/1987 | Hoitink |
| 4,668,512 A | 5/1987 | Lewis et al. |
| 4,678,669 A | 7/1987 | Ricard |
| 4,713,342 A | 12/1987 | Chet et al. |
| 4,724,147 A | 2/1988 | Marois et al. |
| 4,748,021 A | 5/1988 | Chet et al. |
| 4,818,530 A | 4/1989 | Marois et al. |
| 4,828,600 A | 5/1989 | McCabe et al. |
| 4,877,738 A | 10/1989 | Handelsman et al. |
| 4,915,944 A | 4/1990 | Chet et al. |
| 4,952,229 A | 8/1990 | Muir |
| 5,047,239 A | 9/1991 | Pusey |
| 5,049,379 A | 9/1991 | Handelsman et al. |
| 5,068,105 A | 11/1991 | Lewis et al. |
| 5,071,462 A | 12/1991 | Kimura |
| 5,084,272 A | 1/1992 | Speakman et al. |
| 5,194,258 A | 3/1993 | Paau et al. |
| 5,238,690 A | 8/1993 | Elad et al. |
| 5,260,213 A | 11/1993 | Harman et al. |
| 5,266,316 A | 11/1993 | Elad et al. |
| 5,273,749 A | 12/1993 | Bok et al. |
| 5,300,127 A | 4/1994 | Williams |
| 5,344,647 A | 9/1994 | Rossall |
| 5,401,655 A | 3/1995 | Kijima et al. |
| 5,409,509 A | 4/1995 | Burth et al. |
| 5,413,783 A * | 5/1995 | McLaughlin et al. ..... 424/93.51 |
| 5,422,107 A | 6/1995 | Kubota |
| 5,455,028 A | 10/1995 | O'Donnell |
| 5,525,132 A * | 6/1996 | Shanmuganathan ...... 424/93.51 |
| 5,552,138 A | 9/1996 | Handelsman et al. |
| 5,589,381 A | 12/1996 | Nevra et al. |
| 5,614,188 A | 3/1997 | Urano et al. |
| 5,628,144 A | 5/1997 | Eastin |
| 5,632,987 A | 5/1997 | Payne et al. |
| 5,645,831 A | 7/1997 | Chilcott et al. |
| 5,665,354 A | 9/1997 | Neyra et al. |
| 5,667,779 A | 9/1997 | Kubo |
| 5,695,982 A | 12/1997 | Handelsman et al. |
| 5,697,186 A * | 12/1997 | Neyra et al. ................. 47/57.6 |
| 5,702,701 A | 12/1997 | O'Donnell |
| 5,753,222 A | 5/1998 | Marrone et al. |
| 5,852,054 A | 12/1998 | Handelsman et al. |
| 5,869,042 A | 2/1999 | Marrone et al. |
| 5,882,641 A | 3/1999 | Shetty |
| 5,882,915 A | 3/1999 | Howell |
| 5,906,818 A | 5/1999 | Heins et al. |
| 5,916,029 A | 6/1999 | Smith et al. |
| 5,919,447 A | 7/1999 | Marrone et al. |
| 5,922,603 A | 7/1999 | Herrera-Estrella et al. |
| 5,972,689 A | 10/1999 | Cook et al. |
| 5,974,734 A | 11/1999 | Eastin |
| 5,998,196 A | 12/1999 | Handelsman et al. |
| 6,015,553 A | 1/2000 | Germida et al. |
| 6,017,525 A | 1/2000 | Logan et al. |
| 6,030,610 A | 2/2000 | Handelsman et al. |
| 6,033,659 A | 3/2000 | Handelsman et al. |
| 6,103,228 A | 8/2000 | Heins et al. |
| 6,133,196 A * | 10/2000 | Ocamb et al. ............... 504/100 |
| 6,232,270 B1 | 5/2001 | Branly et al. |
| 6,326,016 B2 | 12/2001 | Moesinger |

OTHER PUBLICATIONS

Rosenzweig, W.D. et al., Influence of Environmental Factors on Anatagonism of Fungi by Bacteria in Soil: Clay Minerals and pH, App. and Environ. Micro., Dec. 1979, pp. 1120–1126, vol. 38, No. 6.

Howell, C.R. et al., Mechanisms in the Biocontrol of Rhizoctonia solani–Induced Cotton Seedling Disease by Gliocaldium virens: Antibiosis, Phytopathology, 1995, pp. 469–472, vol. 85, No. 4.

Mao, W. et al., Seed treatment using pre–infiltration and biocontrol agents to reduce damping–off of corn caused by species of Pythium and Fusarium, Plant Disease, Mar. 1998, pp. 294–299, vol. 82, No. 3.

Anon., 'Hidden hunger' threatens many crops, researcher says, Purdue News, Dec. 2000, pp. 1–4.

Anon., Some soil bacteria protect soybeans from disease, 'the paper' Fall Farm Edition, Sep., 2002, p. 7.

Baque, E., Letter from ATCC Central Accessioning Unit, ATCC, May, 2002, pp. 2.

Stratsoy, Interaction of Soybean Roots with Soilborne Pathogens and Nonpathogens, Stratsoy Research Database, 1996?, pp. 1–3.

USDA, Seed's Coat of Many Microbes Wards off Rot, Agricultural Research, Science Update, Apr. 1997, p. 23.

Luo, Y. & Bleakley, B., Biological Control of Fusarium Head Blight (FHB) of Wheat by Bacillus Strains, 1999 National Fusarium Head Blight Control Forum, 1999, p. 60, Biology/Microbiology Dept., Brookings, SD.

Datnoff, L.E. & Pernezny, K.L., Effect of Bacterial and Fungal Microorganisms to Colognize Tomato Roots, Improve Transplant Growth and Control Crown and Root Rot, 2000, pp. 1–8, Southwest Florida Research & Education Center, Univeristy of Florida.

USEPA, Biopesticide Fact Sheet, Bacillus subtilis var. amyloliquefaciens strain FZB24, 5/2000, USEPA Office of Pesticide Programs.

\* cited by examiner

Primary Examiner—Leon B. Lankford, Jr.
(74) Attorney, Agent, or Firm—Robert M. Hunter

(57) ABSTRACT

Fungal/bacterial atagonist combinations, a seed coated with one of the combinations and a plant protected from plant pathogens by one of the combinations. The invention is also a fungal/bacterial antagonist combination and its use for controlling plant pathogens as a biocontrol agent, biopesticide or bio-fungicide.

30 Claims, 2 Drawing Sheets

CONTROLLING PLANT PATHOGENS WITH FUNGAL/BACTERIAL ANATAGONIST COMBINATIONS

CROSS-REFERENCE TO RELATED APPLICATIONS

This application claims the benefit of U.S. Provisional Application No. 60/265,998, filed Feb. 2, 2001, the disclosure of which application is incorporated by reference as if fully set forth herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DMI-9901629 awarded by the National Science Foundation.

BACKGROUND OF THE INVENTION

This invention relates to fungal/bacterial antagonist combinations, a seed coated with said combinations and a plant protected from plant pathogens by said combinations. In particular, the invention relates to fungal/bacterial antagonist combinations and their use for controlling plant pathogens.

Early and late season stalk and root rot are major causes of crop loss. A variety of plants are affected, including tomatoes, peppers, turf grass, soybeans, sunflower, wheat and corn, The pathogens that cause these symptoms include fungi of the genera Fusarium, Phythium, Phytophthora and Penicillium.

One approach to solving the problem of early season damping off of plants is treatment of seeds with fungicides, such as captan, metalaxyl and Maxim. Although these chemicals enhance seed germination and seedling stand by inhibiting the pathogenic ability of Phythium spp. (active in cool, wet soils), they have no activity against the pathogenic fungi that are responsible for late season root and stalk rot.

Fusarium and Penicillium are the pathogens responsible for late season root and stalk rot. These pathogens prefer the warm, dry conditions that occur late in the growing season. There is no chemical or biological fungicide available that addresses the problem of late season root and stalk rot in corn. Currently, the only way to deal with this problem is to periodically rotate to a non-susceptible crop to reduce pathogen numbers. Corn growers can also select hybrids that have better "standability," but such hybrids usually have lower yields. Unfortunately, the corn varieties with the highest yields are usually those most susceptible to late season root and stalk rot.

Trichoderma is a genus of fungi that contains about 20 species. Synonyms for the genus name include Aleurisma and Sporoderma. *Trichoderma virens*, which is also called *Gliocladium virens*, is a member of the genus. The natural habitats of these fungi include soil and plant material. A member of the genus, *Trichoderma harzianum* KRL-AG2 (ATCC 20847) also known as strain T-22, is used as a biocontrol agent that is applied as a seed or soil treatment or on cuttings and transplants. Strains of the species, *Trichoderma virens*, have also been used for control of damping off diseases in plants. For example, *Gliocladium virens* GL-21 is sold under the tradename SoilGard® (formerly GlioGard).

Bacillus is a genus of rod-shaped, gram-positive, aerobic or (under some conditions) anaerobic bacteria. Bacillus species are widely found in soil and water and some have been used to control plant diseases, including root rot. *Bacillus amyloliquefaciens* is a spore-forming member of the genus. *Bacillus amyloliquefaciens* L. L. Cambell strain F (ATCC 23350) is the type strain for the species. Other known and commercially available *Bacillus amyloliquefaciens* strains include those having the following ATCC accession numbers: 23842,23843, 23844 and 23845 (Int. J. Sys. Bacteriol. 37:69–71, 1987; J. Bacteriol. 94:1124–1130, 1967).

*Bacillus lentimorbus* is another spore-forming member of the genus. *Bacillus lentimorbus* Dutky 1940 (ATCC 14707) is the type strain for the species (Skerman, V. B. D., McGowan, V., and Sneath, P. H. A., Approved lists of bacterial names. Int. *J. Syst. Bacteriol.* 30:225–420, 1980). Some researchers consider *Bacillus lentimorbus* to be a variety of *Bacillus popilliae*. *Bacillus lentimorbus* and *Bacillus popilliae* have recently been reclassified as *Paenibacillus lentimorbus* and *Paenibacillus popilliae* (Pettersson, B., Rippere, K. E., Yousten, A. A. and Priest, F. G., Transfer of *Bacillus lentimorbus* and *Bacillus popilliae* to the genus Paenibacillus with emended descriptions of *Paenibacillus lentimorbus* comb. nov. and *Paenibacillus popilliae* comb. nov., Int. *J. yst. Bacterial.* 49: 531–540, 1999). *Bacillus lentimorbus* and *Bacillus popilliae* are the causative agents of milky disease in Japanese beetles and related scarab larvae and "milky spore" powders are sold under the trade names, "Doom," "Milky Spore," "Japidemic" "Grub Killer" and "Grub Attack," for biocontrol of these insects.

Background art biocontrol products have comprised the bacterium *Burkholderia cepacia*, which is also known as *Pseudomonas cepacia*. This bacterium has been implicated as a human pathogen. Furthermore, it has little or no shelf life unless refrigerated at 4 degrees Centigrade at a minimum of 20 percent moisture.

The background art is characterized by U.S. Pat. Nos. 4,476,881; 4,489,161; 4,642,131; 4,668,512; 4,678,669; 4,713,342; 4,724,147; 4,748,021; 4,818,530; 4,828,600; 4,877,738; 4,915,944; 4,952,229; 5,047,239; 5,049,379; 5,071,462; 5,068,105; 5,084,272; 5,194,258; 5,238,690; 5,260,213; 5,266,316; 5,273,749; 5,300,127; 5,344,647; 5,401,655; 5,422,107; 5,455,028; 5,409,509; 5,552,138; 5,589,381; 5,614,188; 5,628,144; 5,632,987; 5,645,831; 5,665,354; 5,667,779; 5,695,982; 5,702,701; 5,753,222; 5,852,054; 5,869,042; 5,882,641; 5,882,915; 5,906,818; 5,916,029; 5,919,447; 5,922,603; 5,972,689; 5,974,734; 5,994,117; 5,998,196; 6,015,553; 6,017,525; 6,030,610; 6,033,659; 6,060,051; and 6,103,228; the disclosures of which patents are incorporated by reference as if fully set forth herein.

Gravely et al. in U.S. Pat. No. 4,476,881 disclose a mixed complementary culture of bacteria and fungi that is used to degrade pectin and cellulose components of tobacco materials. The invention is limited in that it teaches use of different microorganisms for a different purpose.

Papavizas in U.S. Pat. No. 4,489,161 discloses a strain of the fungus *Trichoderma viride* that is an effective biocontrol agent for fusarium wilt of chrysanthemum. The invention is limited in that it teaches use of a different microorganism.

Hoitinik in U.S. Pat. No. 4,642,131 discloses a process for production of a disease-suppressive compost and a microorganism culture for use therein. The invention is limited in that it teaches use of different microorganisms for a different purpose.

Lewis et al. in U.S. Pat. No. 4,668,512 disclose a method for preparing pellets containing living biocontrol fungi and nutrients. The invention is limited in that it teaches a process that involves use of different microorganisms.

Ricard in U.S. Pat. No. 4,678,669 discloses a method of using immunizing commensals to control soil-borne pathogens. The invention is limited in that it teaches use of different microorganisms.

Chet et al. in U.S. Pat. No. 4,713,342 disclose a novel isolate of Trichoderma and it use. The invention is limited in that it teaches use of a different microorganism.

Marois et al in U.S. Pat. No. 4,724,147 disclose a method for preparing pellets containing living biocontrol fungi. The invention is limited in that it teaches a process that involves use of different microorganisms.

Chet et al. in U.S. Pat. No. 4,748,021 disclose antifungal compositions containing Trichoderma active against Fusarium. The invention is limited in that it teaches use of a different microorganism.

Marois et al. in U.S. Pat. No. 4,818,530 disclose a method for preparing pellets containing living biocontrol fungi. The invention is limited in that it teaches a process that involves use of different microorganisms.

McCabe et al. in U.S. Pat. No. 4,828,600 disclose a biological inoculant for corn. The invention is limited in that it teaches use of different microorganisms.

Handelsman et al. in U.S. Pat. No. 4,877,738 disclose a new microorganism culture and a method for biological control of damping off and root rot. The invention is limited in that it teaches a process that involves use of a different microorganism, *Bacillus cereus*.

Chet et al. in U.S. Pat. No. 4,915,944 disclose a novel isolate of Trichoderma and fungicidal compositions containing it. The invention is limited in that it teaches use of a different microorganism.

Muir in U.S. Pat. No. 4,952,229 discloses a soil and foliar supplement. The invention is limited in that it teaches use of different microorganisms.

Pusey in U.S. Pat. No. 5,047,239 discloses a biological control agent for fruit rot. The invention is limited in that it teaches use of a different microorganism for a different purpose.

Handelsman et al. in U.S. Pat. No. 5,049,379 disclose a fungicidal toxin and a method and an inoculum for controlling root rot and damping off. The invention is limited in that it teaches use of a different microorganism, *Bacillus cereus*.

Kimura in U.S. Pat. No. 5,071,462 discloses a method and apparatus for producing an organic fertilizer. The invention is limited in that it teaches use of different microorganisms for a different purpose.

Lewis et al. in U.S. Pat. No. 5,069,105 disclose a fungal formulation for biocontrol of soil-borne plant pathogens. The invention is limited in that it teaches use of different microorganisms.

Speakman et al. in U.S. Pat. No. 5,084,272 disclose a Trichoderma fungus and a fungicide that contains it. The invention is limited in that it teaches use of a different microorganism.

Pauu et al. in U.S. Pat. No. 5,194,258 disclose a method for producing enhanced biocontrol agents. The invention is limited in that it teaches use of different microorganisms.

Elad et al. in U.S. Pat. No. 5,238,690 disclose a novel Trichoderma culture and biological compositions containing it. The invention is limited in that it teaches use of different microorganisms for a different purpose.

Harman et al. in U.S. Pat. No. 5,260,213 disclose fused biocontrol agents. The invention is limited in that it teaches use of different microorganisms.

Elad et al. in U.S. Pat. No. 5,266,316 disclose a novel isolate of Trichoderma harzianum and fungicidal compositions containing it. The invention is limited in that it teaches use of different microorganisms for a different purpose.

Bok et al. in U.S. Pat. No. 5,273,749 disclose a process for preparing coated microbial pesticides and the products of the process. The invention is limited in that it teaches use of different microorganisms.

Williams in U.S. Pat. No. 5,300,127 discloses seed coatings. The invention is limited in that it teaches use of different microorganisms.

Rossall in U.S. Pat. No. 5,344,647 discloses a Bacillus strain that has antimicrobial activity. The invention is limited in that it teaches use of different microorganisms.

Kijima et al. in U.S. Pat. No. 5,401,655 disclose a process for biologically preventing plant diseases. The invention is limited in that it teaches use of different microorganisms for a different purpose.

Kubota in U.S. Pat. No. 5,422,107 discloses a novel fungus and a fungicide containing it. The invention is limited in that it teaches use of a different microorganism.

O'Donnell in U.S. Pat. No. 5,455,028 discloses a method of inhibiting fungi. The invention is limited in that it teaches use of a different microorganism.

Burth et al. in U.S. Pat. No. 5,409,509 disclose a seed treatment. The invention is limited in that it teaches use of different microorganisms.

Handelsman et al. in U.S. Pat. No. 5,552,138 disclose a novel strain of *Bacillus cerus* and a method of protecting plants with the strain. The invention is limited in that it teaches use of a different microorganism.

Neyra et al. in U.S. Pat. No. 5,589,381 disclose a novel strain of *Bacillus licheniformis* that produces an antifungal agent and a use for the strain. The invention is limited in that it teaches use of a different microorganism.

Urano et al. in U.S. Pat. No. 5,614,188 disclose an anti-Fusarium composition containing strains of Bacillus sp. The invention is limited in that it teaches use of different microorganisms.

Eastin in U.S. Pat. No. 5,628,144 discloses solid matrix priming of seeds. The invention is limited in that it teaches use of different microorganisms.

Payne et al. in U.S. Pat. No. 5,632,987 disclose a *Bacillus thuringiensis* toxin that is active against corn rootworm larvae. The invention is limited in that it teaches use of a different microorganism for a different purpose.

Chilcott et al. in U.S. Pat. No. 5,645,831 disclose a *Bacillus thuringiensis* strain and metabolite that are active against corn rootworm. The invention is limited in that it teaches use of a different microorganism for a different purpose.

Neyra et al. in U.S. Pat. No. 5,665,354 disclose a novel strain of *Bacillus licheniformis* that produces an antifungal agent and a use for the strain. The invention is limited in that it teaches use of a different microorganism.

Kubo in U.S. Pat. No. 5,667,779 discloses a fungi-inhibiting composition comprising *Bacillus subtilis*. The invention is limited in that it teaches use of a different microorganism.

Handelsman et al. in U.S. Pat. No. 5,695,982 discloses canavanine-resistant strains of *Bacillus cereus*. The invention is limited in that it teaches use of different microorganisms.

O'Donnell in U.S. Pat. No. 5,702,701 discloses a process for treatment of soil and plants with a composition containing *Bacillus laterosporus*. The invention is limited in that it teaches use of a different microorganism.

Marrone et al. in U.S. Pat. No. 5,753,222 disclose an antibiotic-producing strain of Bacillus and methods of controlling plant diseases with it. The invention is limited in that it teaches use of a different microorganism.

Handelsman et al. in U.S. Pat. No. 5,852,054 disclose fungicidal toxins from a biocontrol bacterium. The invention is limited in that it teaches use of a different microorganism.

Marrone et al. in U.S. Pat. No. 5,869,042 disclose methods for controlling above-ground plant diseases. The invention is limited in that it teaches use of different microorganisms for a different purpose.

Shetty in U.S. Pat. No. 5,882,641 discloses fruit pomice compositions and their uses. The invention is limited in that it teaches use of different microorganisms.

Howell in U.S. Pat. No. 5,882,915 discloses viridiol-deficient strains of Trichoderma virens and process for making and using biocontrol agents that contain them. The invention is limited in that it teaches use of different microorganisms.

Heins et al. in U.S. Pat. No. 5,906,818 disclose a Bacillus mycoides strain for controlling corn rootworm. The invention is limited in that it teaches use of a different microorganism for a different purpose.

Smith et al. in U.S. Pat. No. 5,916,029 disclose a process for producing seeds coated with a microbial composition. The invention is limited in that it teaches use of different microorganisms.

Marrone et al. in U.S. Pat. No. 5,919,447 disclose a strain of Bacillus for controlling plant disease. The invention is limited in that it teaches use of a different microorganism.

Herrera-Estrella et al. in U.S. Pat. No. 5,922,603 disclose a method for obtaining strains of Trichoderma sp. The invention is limited in that it teaches use of a different microorganism.

Cook et al. in U.S. Pat. No. 5,972,689 disclose methods and compositions for control of root diseases. The invention is limited in that it teaches use of different microorganisms.

Eastin in U.S. Pat. No. 5,974,734 discloses solid-matix priming of seeds with microorganisms. The invention is limited in that it teaches use of different microorganisms.

Handelsman et al. in U.S. Pat. No. 5,998,196 disclose a method for suppressing disease using a novel *Bacillus cereus* strain. The invention is limited in that it teaches use of a different microorganism.

Germida et al. in U.S. Pat. No. 6,015,553 disclose a *Bacillus subtilis* strain for controlling pests. The invention is limited in that it teaches use of a different microorganism for a different purpose.

Logan et al. in U.S. Pat. No. 6,017,525 discloses a method of poultry house litter treatment. The invention is limited in that it teaches use of a different microorganism for a different purpose.

Handelsman et al. in U.S. Pat. No. 6,030,610 disclose a novel strain of *Bacillus cereus*. The invention is limited in that it teaches use of a different microorganism.

Handelsman et al. in U.S. Pat. No. 6,033,659 disclose a novel strain of *Bacillus cereus*. The invention is limited in that it teaches use of a different microorganism.

Heins et al. in U.S. Pat. No. 6,103,228 discloses compositions and methods for controlling plant pests and a novel strain of *Bacillus subtilis*. The invention is limited in that it teaches use of a different microorganism.

Branly et al. in U.S. Pat. No. 6,232,270 discloses agricultural compositions containing bacteria. The invention is limited in that it teaches use of different microorganisms and a different process for their use. While the patent suggests that one bacterium that is useful within the disclosed invention is *Bacillus amyloliquefaciens*, it teaches that spores, cultures or suspensions of the bacterium must be combined with an agriculturally effective ingredient of a plant growth stunting agent or herbicide.

Moesinger in U.S. Pat. No. 6,326,016 discloses plant immunization compositions. The invention is limited in that it teaches use of different microorganisms and a different process for their use. While the patent suggests that one bacterium that can be used according to the disclosed invention is *Bacillus amyloliquefaciens*, and that one fungi that can be used according to the invention is Trichoderma spp., it teaches production of an extract by means of biotechnological fermentation process performed by only one microorganism. Furthermore, the patent teaches that high-temperature autoclaving (e.g., one hour at +120 degrees C.) and (optionally) filtering are preferred steps in preparation of the extract.

Background art is also disclosed in the non-patent literature. The StratSoy Research Database posted on the Web (apparently in 1996) a description of a research project entitled Interaction of Soybean Roots with Soilborne Pathogens and Nonpathogens. The project studied the use of *Bacillus amyloliquefaciens* B94 as a biocontrol agent for plant diseases. The invention is limited in that it teaches use of a single different microorganism.

An article entitled Seed's Coat of Many Microbes Wards Off Rot in Science Update section of the April, 1997, issue of Agricultural Research, disclosed the mixing of helpful fungi and bacteria to weaken or kill fungal pathogens that attack young corn sprouts. The applicant believes that the combination used was *T. virens* and *Psuedomonas cepacia*. This invention is limited for two reasons: (1) *P. cepacia* is implicated as causitive in deaths in cystic fibrosis patients and, therefore, EPA registration would probably not be possible, and (2) *P. cepacia* is not a spore-forming bacterium and, therefore, the moisture content of the combination must be maintained at greater than about 17 percent. *T. virens* can be stored and applied at low moisture levels and does not remain in the spore state at the higher moisture levels, making its combination with *P. cepacia* impractical.

In an article authored by L. E. Datnoff et al. entitled Effect of Bacterial and Fungal Microorganisms to Colonize Tomato Roots, Improve Transplant Growth and Control Fusarium Crown and Root Rot that was posted on the Web in 2000 by the University of Florida Southwest Florida Research and Education Center, the authors discuss using a combination of an unidentifed bacterial strain and *Gliocladium virens* to control Fusarium root rot. The invention is limited in,that it teaches use of different microorganisms.

The U.S. Environmental Protection Agency Office of Pesticide Programs posted a Biopesticide Fact Sheet on *Bacillus subtilis* var. *amyloliquefaciens* strain FZB24 (006480) in May, 2000. The fact sheet noted that the strain was approved for use as a growth enhancer and disease suppressor. The invention is limited in that it teaches use of a different microorganism.

No single reference and no combination of the references teach the invention disclosed herein. The background art does not teach combinations of microorganisms disclosed herein, combinations that provide a surprising consistency of performance in plant disease control.

BRIEF SUMMARY OF THE INVENTION

A purpose of the invention is to control the plant pathogens that cause early and late season root and stalk rot. Another purpose is to provide for season-long protection for plants from the pathogens that cause early and late season root and stalk rot. Another purpose is to provide consistent disease control for plants.

One advantage of the invention is that root and stalk rot can be controlled with a composition that is not toxic to humans. Another advantage of the invention is that root and stalk rot can be controlled more economically than with chemical fungicides. Yet another advantage of the invention is that it provides a biocontrol agent or bio-pesticide with extended shelf life. Thus, a seed can be treated with the biocontrol agent and stored for a period of months and still host a viable biocontrol agent that will colonize the root when the seed is placed in the ground, germinates and grows. Furthermore, the disclosed biocontrol agent is competitive with natural soil microbes that occur in the rhizosphere while providing pathogen protection for the plant. A further advantage of the invention is that the combination of a fungal/bacterial antagonist is more effective in controlling fungal pathogens in the plant rhizosphere than either a fungal antagonist or a bacterial antagonist alone, Thus, the invention provides an easy-to-use, effective means of controlling plant pathogens that have been only been controllable by rotation management. A further advantage of the invention is that its use produces more consistent results than the use of either a fungal antagonist or a bacterial antagonist alone, as shown by the Working Examples presented herein. In fact, use of the antagonist combination disclosed herein are shown to be functional when use of its individual constituent antagonists is not.

The invention is an inoculum, a seed coated with the inoculum, a plant protected with the inoculum, a method of producing the inoculum and a method of protecting a seed or a plant with the inoculum. A preferred embodiment of the inoculum comprises a combination of a fungus and a bacterium. Preferably, the fungus is a species of Trichoderma and the bacterium is a species of Bacillus, preferably a spore-forming strain of Bacillus. More preferably, the fungus is *Trichoderma virens* and the bacterium is *Bacillus amyloliquifaciens*, although other combinations are also preferred. Even more preferably, the fungus is *Trichoderma virens* GL-3 (ATCC 58678) and the bacterium is *Bacillus amyloliquefaciens* TJ1000 or 1BE (ATCC BAA-390).

In a preferred embodiment, the inoculum is produced by adding an essentially pure culture, a substantially pure culture, an axenic culture or a biologically pure culture of *Trichoderma virens* GL-3 to a bioreactor containing molasses-yeast extract growth medium using a standard inoculation technique. The medium is agitated and aerated and its temperature is maintained at about 28 degrees Centigrade. After the *Trichoderma virens* GL-3 is grown in the medium for about eight hours, an essentially pure culture, a substantially pure culture, an axenic culture or a biologically pure culture of *Bacillus amyloliquefaciens* TJ1000 or 1BE is added to the medium using a standard inoculation technique. The combined, competitive culture is grown under the aforementioned conditions and produces maximum cell and spore counts in approximately seven days. The combined culture is then used as an inoculum and is applied each seed at a rate of no less than about 1,000 spore counts per seed.

In another preferred embodiment, a solution containing an essentially pure culture, a substantially pure culture, an axenic culture or a biologically pure culture of the fungal antagonist *Trichoderma virens* GL-3 is combined with a solution containing an essentially pure culture, a substantially pure culture, an axenic culture or a biologically pure culture of *Bacillus amyloliquefaciens* TJ1000 or 1BE in a 50/50 mixture by volume and is applied to a seed at a rate of no less than about 10,000 spore counts per seed.

In broad terms, a preferred embodiment of the invention is an agricultural inoculum suitable for inoculating plant seeds comprising a fungal antagonist selected from the group consisting of *Trichoderma virens* GL-3 (ATCC 58678) and mutants thereof, a bacterial antagonist selected from the group consisting of *Bacillus amyloliquefaciens* TJ1000 or 1 BE (ATCC BAA-390) and mutants thereof, and a suitable carrier that is non-phytotoxic, non-bacteriostatic, and non-bacteriocidal.

Another preferred embodiment of the invention is a composition of matter comprising a plant seed inoculated with a combination comprising a fungal antagonist selected from the group consisting of *Trichoderma virens* GL3 (ATCC 58678) and mutants thereof and a bacterial antagonist selected from the group consisting of *Bacillus amyloliquefaciens* TJ1000 or 1BE (ATCC BAA-390) and mutants thereof, wherein said combination suppresses growth of plant pathogenic fungi.

Yet another preferred embodiment of the invention is a seed or plant inoculated with a combination comprising a fungal antagonist selected from the group consisting of *Trichoderma virens* GL-3 (ATCC 58678) and mutants thereof and a bacterial antagonist selected from the group consisting of *Bacillus amyloliquefaciens* TJ1000 or 1BE (ATCC BAA-390) and mutants thereof, wherein the combination suppresses growth of plant pathogenic fungi.

In broad terms, a preferred embodiment of the invention is a method of protecting a plant from disease caused by a plant pathogenic fungus comprising inoculating seeds from said plant with a combination comprising a fungal antagonist selected from the group consisting of *Trichoderma virens* GL-3 (ATCC 58678) and mutants thereof and a bacterial antagonist selected from the group consisting of *Bacillus amyloliquefaciens* TJ1000 or 1BE (ATCC BAA-390) and mutants thereof, wherein said combination suppresses growth of plant pathogenic fungi.

Another preferred embodiment of the invention is a method of protecting a seed or a plant from disease caused by a plant pathogenic fungus comprising inoculating seeds from said plant with a composition comprising a spore-forming fungal antagonist and a spore-forming bacterial antagonist. Preferably, the spore-forming bacterial antagonist is selected from the group *Bacillus amyloliquefaciens* TJ1000 or 1BE (ATCC BAA-390) and mutants thereof.

Another preferred embodiment of the invention is a method of protecting a seed or a plant from disease caused by a plant pathogenic fungus comprising inoculating seeds from said plant with a composition comprising a fungal antagonist and a bacterial antagonist, wherein said combination suppresses growth of plant pathogenic fungi. A preferred embodiment is capable of control of the plant pathogen fungi Fusarium, Phythium, Phytophthora and Penicillium.

Another preferred embodiment of the invention is a method of protecting a plant from disease caused by a plant pathogenic fungus comprising inoculating seeds from said plant with a composition comprising a fungal antagonist and a bacterial antagonist selected from the group consisting of *Bacillus amyloliquefaciens* TJ1000 or 1BE (ATCC BAA- 390) and mutants thereof, wherein said combination suppresses growth of plant pathogenic fungi.

Yet another preferred embodiment of the invention is a method for biologically controlling or inhibiting stalk rot or root rot comprising coating seeds with an effective amount of a composition comprising *Trichoderma virens* GL-3 (ATCC 58678) and *Bacillus amyloliquefaciens* TJ1000 or 1BE (ATCC BAA-390).

A further preferred embodiment of the invention is process for making a composition comprising introducing an essentially pure culture of *Bacillus amyloliquefaciens* TJ1000 or 1BE (ATCC BAA-390) to a growth medium about eight hours after an essentially pure culture of *Trichoderma virens* GL-3 (ATCC 58678) is introduced to the growth medium and growing the culture as a competitive culture.

Another preferred embodiment of the invention is a process comprising making a composition by combining an essentially pure culture of *Trichoderma virens* GL-3 (ATCC 58678) with an essentially pure culture of *Bacillus amyloliquefaciens* TJ1000 or 1BE (ATCC BAA-390) in a 50:50 mixture and applying said composition to a seed at a rate of at least 100,000 spores per seed.

A further preferred embodiment of the invention is a method for protecting plants in a growing medium from damping off and root rot fungal plant disease comprising placing in the growing medium in the immediate vicinity of the plant to be protected an effective quantity of one of the fungal/bacterial combinations disclosed herein.

Yet another preferred embodiment of the invention is a method for protecting plants from fungal plant disease comprising adding one of the fungal/bacterial combinations disclosed herein in an effective quantity to a substrate such as pelletized calcium sulfate or pelletized lime and placing the pellet in the immediate vicinity of the plant to be protected. The pellet may or may not contain other nutrients.

Another preferred embodiment of the invention is a method for protecting plants from fungal plant disease comprising adding one of the fungal/bacterial combinations disclosed herein in an effective quantity to a liquid solution such as water and applying the liquid solution in the immediate vicinity of the plant to be protected. The liquid may or may not contain additional nutrients and may include a chemical fungicide applied to the seed such as, for example, Maxim or captan. The disclosed combination may also be added to a plant nutrient (nitrogen-phosphorus-potassium (NPK)) plus plant micro-nutrient solution that is compatible with the combination and applied as an in-furrow treatment.

A further preferred embodiment of the invention is a method for biologically controlling a plant disease caused by a plant-colonizing fungus, the method comprising inoculating a seed of the plant with an effective amount of a microbial inoculant comprising a combination of microorganisms having all of the identifying characteristics of *Trichoderma virens* Gl-3 and *Bacillus amyloliquefaciens* TJ1000 or 1BE, said inoculation resulting in the control of said plant disease. The invention is also a method according to the above preferred embodiment wherein said inoculation results in the control of more than one plant disease.

Yet another preferred embodiment of the invention involves combining of a spore forming fungal strain and a spore forming bacterial strain to enhance ease of use and longevity of shelf life both as a stored product and when applied to a seed. In another preferred embodiment, the invention involves applying the disclosed Trichoderma microorganism and the Bacillus microorganism to a wettable powder, in which form it is applied.

Another preferred embodiment of the invention is composition of matter made by combining: a fungal antagonist selected from the group consisting of *Trichoderma virens* GL-3 (ATCC 58678) and mutants thereof; a bacterial antagonist selected from the group consisting of *Bacillus amyloliquefaciens* TJ1000 or 1BE (ATCC BAA-390) and mutants thereof; and a suitable carrier that is non-phylotoxic, non-bacteriostatic, and non-bacteriocidal.

A further preferred embodiment of the invention is an antagonist for controlling plant pathogens made by combining effective amounts of: a fungal antagonist selected from the group consisting of *Trichoderma virens* GL-3 (ATCC 58678) and mutants thereof; a bacterial antagonist selected from the group consisting of *Bacillus amyloliquefaciens* TJ1000 or 1BE (ATCC BAA-390) and mutants thereof; and a suitable carrier that is non-phytotoxic, non-bacteriostatic, and non-bacteriocidal.

Yet another preferred embodiment of the invention is a seed assembly made by combining a plant seed with effective amounts of a spore-forming bacterial antagonist and a spore-forming fungal antagonist. In a preferred embodiment, the seed is a seed of a plant selected from the group consisting of a monocot, and a dicot. In another preferred embodiment, the seed is a seed of a plant selected from the group consisting of a legume plant, and a non-legume plant. In another preferred embodiment, the seed is a seed of a plant selected from the group consisting of corn, sunflower, soybean, field pea, and wheat.

Another preferred embodiment of the invention is method for culturing a plant comprising: applying an antagonist disclosed herein to a seed or to the seedbed of the plant; planting the seed in the seedbed; growing the plant to yield a crop; and harvesting the crop; wherein said applying step increases the yield of the crop. In another preferred embodiment, the antagonist is applied to the seed or to the seedbed of a plant selected from the group consisting of a monocot, and a dicot. In another preferred embodiment, the antagonist is applied to the seed or to the seedbed of a plant selected from the group consisting of a legume plant, and a non-legume plant. In another preferred embodiment, the antagonist is applied to the seed or to the seedbed of a plant selected from the group consisting of corn, sunflower, soybean, field pea, and wheat.

Yet another preferred embodiment is a process comprising: making a composition by combining an essentially pure culture of *Trichoderma virens* GL-3 (ATCC 58678) with an essentially pure culture of *Bacillus amyloliquefaciens* TJ1000 or 1BE (ATCC BAA-390) in a mixture; and applying said composition to a seed; wherein said mixture ranges in composition from 10 to 90 percent *Trichoderma virens* GL-3 (ATCC 58678) by volume and from 90 to 10 percent *Bacillus amyloliquefaciens* TJ1000 or 1BE (ATCC BAA-390) by volume.

Yet another preferred embodiment of the invention is a process comprising: making a composition by combining an essentially pure culture of *Trichoderma virens* GL-3 (ATCC 58678) with a plurality of essentially pure cultures of bacteria in a mixture; and applying said composition to a seed; wherein said mixture ranges in composition from 10 to 90 percent *Trichoderma virens* GL-3 (ATCC 58678) by volume.

A further preferred embodiment of the invention is an antagonist for controlling plant pathogens made by combining effective amounts of: a fungal antagonist selected from the group consisting of a strain of *Trichoderma virens* and mutants thereof; a bacterial antagonist selected from the group consisting of *Bacillus amyloliquefaciens* TJ1000 or 1BE (ATCC BAA-390) and mutants thereof; and a suitable carrier that is non-phytotoxic, non-bacteriostatic, and non-bacteriocidal. Preferably, the strain is *Trichoderma viren* Gl 21, which is presently EPA registered.

In a preferred embodiment, the invention is an antagonist for controlling plant pathogens made by combining effective amounts of: a fungal antagonist selected from the group consisting of *Trichoderma virens* GL-3 (ATCC 58678) and mutants thereof; a plurality of bacterial antagonists; and a suitable carrier that is non-phytotoxic, non-bacteriostatic, and non-bacteriocidal. Preferably, the plurality of bacterial antagonists comprises a strain of *Erwinia carotovora* and/or a strain of *Bacillus lentimorbus*.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings.

DETAILED DESCRIPTION OF THE INVENTION

Figure 1:
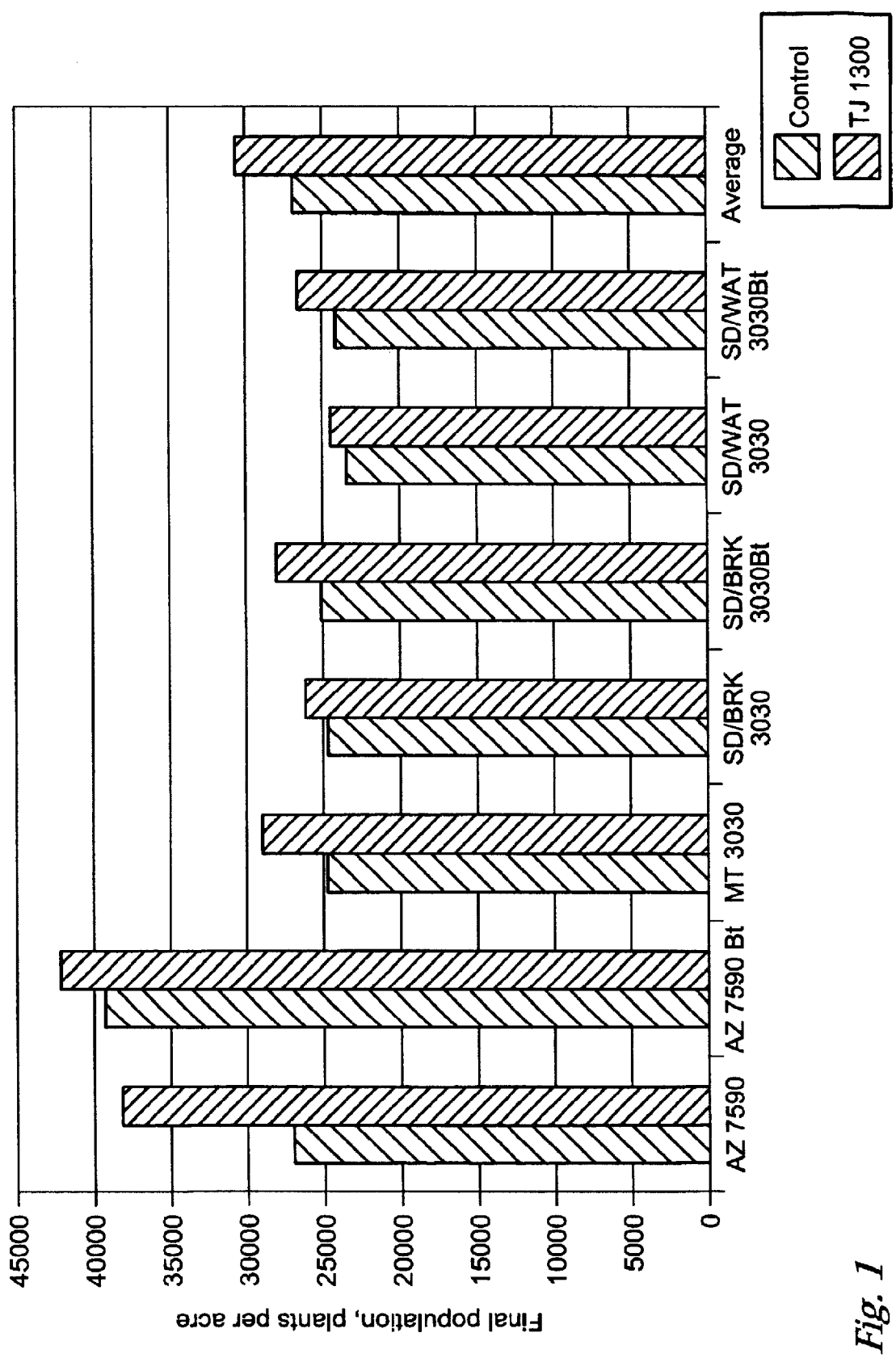
FIG. 1 is a plot that compares the incidence of stalk rot in TJ1300-treated plots versus the incidence of stalk rot in control plots.

A preferred embodiment of the invention comprises the fungus *Trichoderma virens* GL-3 (ATCC 58678). This microorganism may be obtained from the American Type Culture Collection (ATCC), 12301 Parklawn Drive, Rockville, Md., 20852-1776.

A preferred embodiment of the invention also comprises the bacterium *Bacillus lentimorbus* TJ 1000, which is renamed herein *Bacillus amyloliquefaciens* TJ1000 or 1BE, based on a more accurate determination of the name of Bacillus species that occurred during the pendency of the provisional patent application incorporated by reference above. This microorganism was deposited with the ATTC on Oct. 31, 2001, during the pendency of the provisional patent application incorporated by reference above, and was assigned accession number ATCC BAA-390. This deposit has been made under conditions that specify that access to the deposit will be available during the pendency of this patent application (or any non-provisional application relying on this application for priority or continuation, division, or continuation-in-part thereof) to one determined by the Director of the U.S. Patent and Trademark Office to be entitled thereto under 37 CFR 1.14 and 35 U.S.C. 122 and that all restrictions on the availability to the public of the deposit will be irrevocably removed upon the granting of a patent on any of the aforementioned applications.

A preferred embodiment of the invention involves combining an essentially pure culture of *Trichoderma virens* GL-3 (ATCC 58678) and an essentially pure culture of *Bacillus amyloliquefaciens* TJ1000 or 1BE (ATCC BAA-390) in a competitive culture process. The competitive culture process involves adding the *Bacillus amyloliquefaciens* TJ1000 or 1BE (ATCC BAA-390) to a growth medium about eight hours after the *Trichoderma virens* GL-3 (ATCC 58678) was added to the medium. The combined culture is then applied to a seed, for example, a corn seed. The combination grown in a competitive culture provides protection for seeds and plants and is especially effective in a high-stress, high-fungal pathogen environment during the early stages of plant development.

Another preferred embodiment of the invention involves growing an essentially pure culture of *Trichoderma virens* GL-3 (ATCC 58678) and an essentially pure culture of *Bacillus amyloliquefaciens* TJ1000 or 1BE (ATCC BAA-390) separately for five days. After the cultures are grown separately, the compositions that contain them are combined in a 50/50 combination by volume and then the combination is applied to a seed, for example, a corn seed. The combined cultures are applied to a seed provides protection for seeds and plants from fungal pathogens. This combination is especially effective under conditions that are less stressful to the plant.

A preferred step in the process involves applying either of the above combinations to a seed involves adding an aqueous solution comprising 30 grams/liter of molasses to the solution containing the combination to produce an appropriate spore count in the resulting composition. The resulting composition is then applied to the seed as a liquid mist to achieve optimum application rates per seed using the molasses as an adhesive to adhere the spores to the seed.

In a preferred embodiment, the bioreactor used to culture the microorganism cultures is a New Brunswick Bioflow III bioreactor. For optimal results, the agitation setting of the bioreactor is set at about 350 rpm, the aeration setting of the bioreactor is set at about 3.0 with an aeration air pressure of about 15 pounds per square inch and the temperature setting is set at about 28 degrees Centigrade. The preferred growth medium for each of the individual cultures and the combined competitive culture comprises about 30 grams per liter of molasses and about 5 grams per liter of yeast extract and is referred to as a MYE medium. In another preferred embodiment, the medium contains about 5 milliliters of antifoam. In a preferred embodiment, spore production is measured by counting spores using a hemacytometer manufactured by Hausser Scientific.

A variety of seed treatments or no seed treatment may be practiced before the seed is inoculated with the disclosed inoculum. In some preferred embodiments, seed treatments include osmotic priming and pre-germination of the seed. Because *Trichoderma virens* GL-3 and *Bacillus amyloliquefaciens* TJ1000 or 1BE are spore formers, the disclosed inoculum does not require high moisture levels for survival and, therefore, can be applied to seed and other materials without a sticker, such as those sold under the trade names Pelgel (LipaTech), Keltrol (Xanthan) Cellprill or Bond.

In a preferred embodiment, the invention involves combining of a spore forming fungal strain and a spore forming bacterial strain to enhance ease of use and longevity of shelf life both as a stored product and when applied to a seed. In another preferred embodiment, the invention involves applying the disclosed Trichoderma microorganism and the disclosed Bacillus microorganism to a wettable powder, and marketing the wettable powder.

WORKING EXAMPLE NO. 1

Greenhouse testing was conducted to determine the effectiveness of the disclosed biocontrol agents. Treated and untreated corn seeds were grown in soil infested with seven percent Fusarium infested wheat seed. In this testing, the following treatment codes were used:

CONTROL—Nothing on the seed

TJ1000—*Bacillus amyloliquefaciens* TJ1000 or 1BE

TJ0300—*Trichoderma virens* GL-3

TJ1300—50/50 combination of *Trichoderma virens* GL-3 and *Bacillus amyloliquefaciens* TJ1000 or 1BE TJ1310—competitive culture of *Trichoderma virens* GL-3 and *Bacillus amyloliquefaciens* TJ1000 or 1BE, resulting in a 70/30 ratio of Trichoderma to Bacillus The results of greenhouse testing are presented in Table 0. The rating scale used was 9=worst plant protection and 1=best plant protection. Seed treated with biocontrol organisms grown in competitive culture showed an increase in plant protection over seed treatments with the same biological control organisms grown in non-competitive culture. The biocontrol agents were applied to the seed without a sticker.

TABLE 0

Greenhouse Testing Results

| Treatment | Replication 1 | Replication 2 | Replication 3 | Average |
|---|---|---|---|---|
| Control | 9 | 7 | 6 | 7.3 |
| TJ 0300 | 6 | 5 | 5 | 5.3 |
| TJ 1000 | 7 | 6 | 5 | 6 |
| TJ 1300 | 6 | 5 | 6 | 5.6 |
| TJ 1310 | 1 | 3 | 3 | 2.3 |

WORKING EXAMPLE NO. 2

In a subsequent experiment, field trials were conducted at seven locations throughout the U.S. Site locations included Arizona, Colorado, Kansas, Montana, North Dakota and two South Dakota locations. At each location, the trial contained a CONTROL that was treated with the industry-standard chemical treatment, MAXIM. All cultures used in the trial were grown in MYE broth for five days. *Bacillus amyloliquefaciens* TJ1000 or 1BE was cultured individually (non-competitive) and with *Trichoderma virens* GL-3 (competitive culture). *Trichoderma virens* GL-3 and *Bacillus amyloliquefaciens* TJ1000 or 1BE were also grown in non-competitive culture were also applied to the same seed to test the effectiveness of non-competitive culture versus competitive culture. Corn seeds were treated to give a final concentration of 1,000,000,000 bacterial/fungal spores per acre. Seed treatment was done with a Gustafson benchtop seed treater, Model BLT.

The plot location in Kansas was severely damaged by early dry conditions and the plot was terminated prior to harvest. The Colorado location was damaged due to machine damage prior to harvest. Colorado yield data were collected but were extremely variable and were not included in the analyzed data set. The Colorado stalk rot data were included in the data set The value of the Stalk Rot variable was determined by counting ten plants in a row, determining the number of root rot/stalk rot infected plants and expressing that number as a percentage. As illustrated in FIG. 1, in six trials, the average infection rate in the control was 55.13 percent versus 38.62 percent in the entries treated with the fungal/bacterial combination, TJ1300. The data revealed an average reduction of disease incidence of 30 percent with the Colorado location showing a reduction of over 60 percent.

Figure 2:
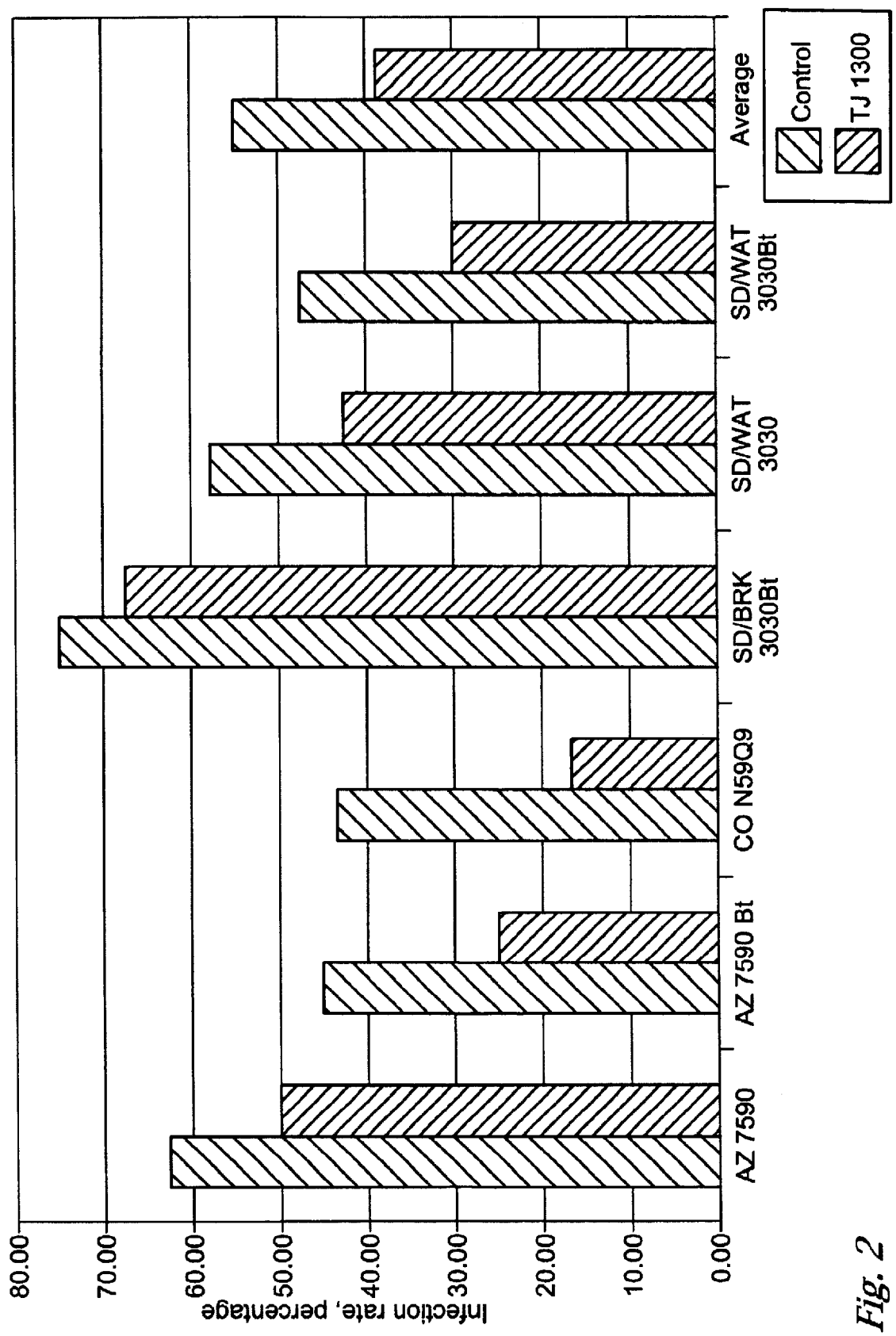
FIG. 2 is a plot that compares final plant populations in TJ1300-treated plots versus final plant populations in control plots.

The value of the Final Population variable was determined by a conducting a physical count of the plants in a measured area and converting to a per acre count. As illustrated in FIG. 2, the average increase in final plant population was 3,742 plants per acre or an increase of 12.2 percent. This increased population was the result of controlling the disease early and having less plant death throughout the season.

Use of TJ1300 resulted in an average yield benefit of 5.35 bushels per acre. Average yield was determined from eight trials: 4 in South Dakota, 1 in North Dakota, 2 in Arizona, and 1 in Montana.

WORKING EXAMPLE NO. 3

Greenhouse Methods: All test cultures were grown in MYE (three percent Molasses, 0.5 percent Yeast Extract) broth for five days. Bacteria were grown up individually (non-competitive) and with *T. virens* GL-3 (competitive culture). *T virens* GL-3 was also grown in a non-competitive culture for testing. *T. virens* GL-3 and test bacteria grown in non-competitive culture were also applied to the same seed to test the effectiveness of non-competitive culture versus competitive culture. Corn seeds were treated to give a final concentration of $1\times10^9$ bacteria/fungal spores (may also be referred to a Colony Forming Units or CFU) per acre. Seed treatment was done with a Gustafson Benchtop Seed Treater, Model BLT. Seeds were grown in soil infested with seven percent Fusarium-infested wheat seed. After four weeks, plant heights were taken as well as plant biomass. Plant heights were taken by measuring from the soil line to the tallest leaf, biomass of the plants was taken by cutting the plants at the soil line and then weighing plants on analytical scale. The treatment matrix was as follows:

Control—No pathogen added to soil.

Control—With pathogen added to soil.

TJ1000—*Bacillus amylotiquefaciens* TJ1000 or 1BE

TJ0300—*Trichoderma virens* GL-3

TJ2000—*Erwinia carotovora*

TJ1300—*B. amyloliquefaciens* TJ1000 or 1BE and *T. virens* GL-3 (non-competitive)

TJ2300—*E. carotovora* and *T. virens* GL-3 (non-competitive)

TJ1310—*B. amyloliquefaciens* TJ1000 or 1BE and *T. virens* GL-3 (competitive)

TJ1-2310—*B. amyloliquefaciens* TJ1000 or 1BE, *E. carotovora* and *T. virens* GL-3 (competitive)

TJ2310—*E. carotovora* and *T. virens* GL-3 (competitive)

Determination of CFU (Colony Forming Units) concentrations in competitive cultures: Competivtive cultures grown for five days. CFU counts of each organism were performed using a hemacytometer (Hausser Scientific) under light microscopy 5000x magnification. This method was used to determine the CFU counts in the greenhouse and field trials.

Enumeration through plate counts: Competitive cultures were grown for five days in submerged culture then 200 milliliters (ml) of the culture was harvested and aliquoted into four 50 ml centrifuge tubes. After centrifugation at 10,000 revolutions per minute (rpm) for 10 minutes resulting pellets were washed twice in equal volumes of $D_2H_2O$. Pellets were then re-suspended in 25 ml of saline. One ml samples were diluted $10^{-1}$ to $10^{-8}$ and plated onto potato dextrose agar (PDA) plates. Colonies are then counted and corrolated back to the dilution rates to determine CFU per ml of culture broth.

Results: All of the biocontrol agents in this experiment produced significant plant biomass increases over the pathogen-treated control and all of the treatments were numerically greater than the control plants in soil that contained no pathogen. The effects of bacterial/fungal combination TJ1310 and the bacterial treatment TJ1000 were significantly greater than both controls in the experiment.

Table 1. Demonstration of the Effectiveness of Biological Combinations and Individual Bacteria and Individual Fungal Treatments on Increasing the Biomass of Greenhouse-Grown Corn Seedlings in Pathogen-Treated Soil vs. the Untreated Control

| Treatment | Ratio | Rank | Biomass (grams) |
|---|---|---|---|
| Control Path | 0/0 | 10 | 3.62 a |
| Control No Path | 0/0 | 9 | 7.25 ab |
| TJ 1300 | 50/50 | 8 | 8.67 b |
| TJ 2310 | 30/70 | 7 | 9.04 b |
| TJ 2000 | 100/0 | 6 | 10.73 b |
| TJ 1-2310 | 20/20/60 | 5 | 11.37 b |
| TJ 2300 | 50/50 | 4 | 11.41 b |
| TJ 0300 | 0/100 | 3 | 11.53 b |
| TJ 1310 | 30/70 | 2 | 12.24 bc |
| TJ 1000 | 100/0 | 1 | 12.89 bc |
| CV % | | | 33.9 |
| LSD (0.05) | | | 4.55 |

WORKING EXAMPLE NO. 4

Materials and Methods: A field trial was conducted using the corn variety NK 3030Bt using the following biological treatments of the seed at a rate of approximately $10^6$ CFU per seed. The seed was planted at a seeding rate of 25,000 seeds per acre in 30-inch rows in a randomized, replicated block. Each entry was replicated four times. The pathogen levels were natural populations at a location near Groton, S.Dak. The entries were as follows:

Control: Maxim Seed treatment (Maxim is a trademark of Syngenta Crop Protection)

TJ 1000—*Bacillus amyloliquefaciens* TJ1000 or 1BE

TJ 0300—*Trichoderma virens* GL-3

TJ 1300—50/50 combination of *B. amyloliquefaciens* TJ1000 or 1BE and *T. virens* GL-3

TJ 1310—Coculture 30/70 combination of *B. amyloliquefaciens* TJ1000 or 1BE and *T. virens* GL-3

TJ 66/300—50/50 combination of *Bacillus amyloliquefaciens* TJ1000 or 1BE and *T. virens* GL-3

Results: The trial produced significant yield response over the control with the entries TJ 0300, TJ 1300, and TJ 1310. The combinations TJ 1300 and TJ 1310 produced a yield response numerically greater than that of TJ 0300. The effects of bacterial/fungal combination TJ 66/300 and the bacterial treatment TJ 1000 were numerically greater than the control but not significantly greater. The results are presented in Table 2.

Conclusion: The bacterial/fungal combinations of entries TJ 1300 and TJ 1310 are the most effective biocontrol treatments in the trial for increasing the yield of corn.

TABLE 2

Effect of Biological Seed Treatment on Yield of Corn Variety N3030 Bt under Field Conditions.

| Treatment | Ratio | Rank | Location | Trial | Yield |
|---|---|---|---|---|---|
| Control Maxim | 0/0 | 6 | Groton, SD | Seed Treat | 164.8 a |
| TJ 1000 | 100/0 | 4 | Groton, SD | Seed Treat | 175.1 ab |
| TJ 0300 | 0/100 | 3 | Groton, SD | Seed Treat | 179.5 bc |
| TJ 1300 | 50/50 | 2 | Groton, SD | Seed Treat | 183.3 bc |
| TJ 1310 | 30/70 | 1 | Groton, SD | Seed Treat | 189.8 c |
| TJ 66/300 | 50/50 | 5 | Groton, SD | Seed Treat | 173.2 ab |
| CV % | | | | | 13.54 |
| LSD (0.05) | | | | | 12.5 |

WORKING EXAMPLE NO. 5

Material and Methods: A field trial was conducted using the corn variety NK 3030Bt using the following biological treatments of the seed at a rate of approximately $10^6$ CFU per seed. The seed was planted at a seeding rate of 25,000 seeds per acre in 30-inch rows in a radomized replicated block. Each entry was replicated four times. The pathogen levels were natural populations at a location near Groton, S.Dak. The entries were as follows:

Control: Maxim Seed treatment (Maxim is a trademark of Syngenta Crop Protection)

TJ 1300—50/50 combination of *B. amyloliquefaciens* TJ1000 or 1BE and *T. virens* GL-3

Result: As indicated in Table 3, the trial produced a significant response in the yield of the seed treated with the biocontrol agent TJ 1300 (described above) as compared with the untreated control.

TABLE 3

Effect of Biological Seed Treatment on Yield of Corn Variety NK 3030 Bt under Field Conditions.

| Treatment | Ratio | Rep | Location | Yield |
|---|---|---|---|---|
| Control | 0/0 | 1 | Groton, SD | 156.8 |
| Control | 0/0 | 2 | Groton, SD | 163.3 |
| Control | 0/0 | 3 | Groton, SD | 151.0 |
| Average | 0/0 | | Groton, SD | 157.03 a |
| 1300 | 50/50 | 1 | Groton, SD | 184.3 |
| 1300 | 50/50 | 2 | Groton, SD | 179.1 |
| 1300 | 50/50 | 3 | Groton, SD | 177.3 |
| Average | 50/50 | | Groton, SD | 180.21 b |
| CV % | | | | 5.65 |
| LSD (0.05%) | | | | 9.04 |

WORKING EXAMPLE NO. 6

Materials and Methods: A field trial was conducted using the corn variety NK2555 using the TJ 1300 (50/50 combination of *B. amyloliquifactiens* TJ1000 or 1BE and *T. virens* GL-3) biological treatments of the seed at variable rates. The purpose of the trial was to identify the most effective application rate for the bacterial/fungal combination of TJ 1300. The 1× rate was approximately $1 \times 10^6$ CFU per seed. The seed was planted at a seeding rate of 25,000 seeds per acre in 30-inch rows in a randomized, replicated block. Each entry was replicated four times. The pathogen levels were natural populations at a location near Groton, S.Dak. The entries were as follows:

Control—Maxim (Maxim is a trademark of Syngenta Crop Protection)
- 0.5× rate
- 1× rate
- 1.5× rate
- 2× rate Results: All of the biocontrol treatments in this experiment resulted in significant yield response over the control with the 1.5× rate producing significantly better results than the 2× rate. The results of this trial, presented in Table 4, indicated that the most efficacious application rate of the biocontrol agent TJ 1300 was approximately $1.5 \times 10^6$ per seed.

TABLE 4

Effect of TJ 1300 Biological Seed Treatment on Yield of Corn Variety N2555 at Variable Rates

| Treatment | Ratio | Rank | Location | Trial | Yield |
|---|---|---|---|---|---|
| Control | 0/0 | 5 | Groton, SD | Rate | 140.2 a |
| 0.5× rate | 50/50 | 3 | Groton, SD | Rate | 153.6 bc |
| 1× rate | 50/50 | 2 | Groton, SD | Rate | 156.2 bc |
| 1.5× rate | 50/50 | 1 | Groton, SD | Rate | 161.1 c |
| 2× rate | 50/50 | 4 | Groton, SD | Rate | 152.07 b |
| CV % | | | | | 5.31 |
| LSD (0.05%) | | | | | 8.61 |

WORKING EXAMPLE NO. 7

Materials and Methods: Field trials were conducted using the corn varieties NK 3030 and NK 3030Bt at a location in Brookings, S.Dak. and NK 3030Bt and NK2555 at a location in Groton, S.Dak. The purpose of the trial was to compare pathogen control of liquid biocontrol preparations to a control treated with only water. The results of the trial were quantified in yield of corn in bushels per acre. The water was applied to the control at a 10 gallon per acre rate. Biocontrol treatments were prepared by adding $1 \times 10^8$ CFU per gram of a wettable powder (Mycotech, Inc.). Two and one half grams of the wettable powder was added per one gallon of water and soil applied in the seed furrow at a rate of 10 gallons per acre. The seed was Maxim (Maxim is a trademark of Syngenta Crop Protection) treated and was planted at a seeding rate of 25,000 seeds per acre in 30-inch rows in a randomized, replicated block. Each entry was replicated four times. The pathogen levels were natural populations at each location. The entries were as follows:

Control—Water

TJ 1000—*Bacillus amyloliquifaciens* TJ1000 or 1BE

TJ 0300—*Trichoderma virens* GL-3

TJ 1300—50/50 combination of *B. amyloliquifaciens* TJ1000 or 1BE and *T. virens* GL-3

TJ 1310—Coculture 30/70 combination of *B. amyloliquifaciens* TJ1000 or 1BE and *T. virens* GL-3

TJ 66/300—50/50 combination of *Bacillus lentimorbus* and *T. virens* GL-3

Results: Table 5 shows a significant yield increase to the biocontrol treatments of TJ 1000, TJ1300, and TJ 66/300. All of the biocontrol treatments showed a numerical yield increase.

Table 6 shows a significant yield increase to the biocontrol treatments of TJ1000, TJ0300, and TJ1300. Again, all of the biocontrol treatments showed a numerical yield increase.

Table 7 shows no significance in the yield between the treatments and the control, however, the yield of TJ0300 was numerically less than the control by over 10 bushels per acre and is significantly less than the yields of the TJ1000 and TJ 1310 bacterial/fungal combination. This table demonstrates the strength of the disclosed bacterial/fungal combinations over the fungal control alone.

Table 8 shows the treatments of TJ 1000 and TJ 66/300 with significantly less yield than the control while the treatments of TJ0300, TJ1300, and TJ1310 having no significant difference. In this trial, it was the bacterial entry of TJ1000 alone that shows weakness in pathogen control. This table demonstrates the strength of disclosed bacterial/fungal combinations over the bacterial treatment alone.

Conclusion: The bacterial/fungal combination of entries TJ 1300 and TJ 1310 produce consistent pathogen control and/or yield response, while the bacteria entry of TJ 1000 alone and fungal entry of TJ 0300 alone produce inconsistent pathogen control and/or yield response.

TABLE 5

Liquid Drench Treatment on Corn Variety NK3030 at Brookings, SD Location

| Treatment | Variety | Ratio | Rank | Location | Trial | Yield |
|---|---|---|---|---|---|---|
| Control | NK3030 | 0/0 | 6 | Brookings, SD | Liquid | 162.2 a |
| TJ1000 | NK3030 | 100/0 | 1 | Brookings, SD | Liquid | 179.7 b |
| TJ0300 | NK3030 | 0/100 | 5 | Brookings, SD | Liquid | 170.7 ab |
| TJ1300 | NK3030 | 50/50 | 2 | Brookings, SD | Liquid | 177.9 b |
| TJ1310 | NK3030 | 30/70 | 4 | Brookings, SD | Liquid | 172.8 ab |
| TJ66/300 | NK3030 | 50/50 | 3 | Brookings, SD | Liquid | 175.0 b |
| CV % | | | | | | 7.38 |
| LSD (0..20%) | | | | | | 12.36 |

TABLE 6

Liquid Drench Treatment on Corn Variety NK2555 at Groton, SD Location

| Treatment | Variety | Ratio | Rank | Location | Trial | Yield |
|---|---|---|---|---|---|---|
| Control | NK2555 | 0/0 | 6 | Groton, SD | Liquid | 136.2 a |
| TJ1000 | NK2555 | 100/0 | 1 | Groton, SD | Liquid | 147.7 c |
| TJ0300 | NK2555 | 0/100 | 2 | Groton, SD | Liquid | 145.0 bc |
| TJ1300 | NK2555 | 50/50 | 3 | Groton, SD | Liquid | 142.5 bc |
| TJ1310 | NK2555 | 30/70 | 4 | Groton, SD | Liquid | 141.5 abc |
| TJ66/300 | NK2555 | 50/50 | 5 | Groton, SD | Liquid | 138.5 abc |
| CV % | | | | | | 10.92 |
| LSD (0.20%) | | | | | | 8.42 |

TABLE 7

Liquid Drench Treatment on Corn Variety NK3030 at Brookings, SD Location

| Treatment | Variety | Ratio | Rank | Location | Trial | Yield |
|---|---|---|---|---|---|---|
| Control | NK3030Bt | 0/0 | 4 | Brookings, SD | Liquid | 181.5 ab |
| TJ1000 | NK3030Bt | 100/0 | 2 | Brookings, SD | Liquid | 185.5 b |

TABLE 7-continued

Liquid Drench Treatment on Corn Variety NK3030 at Brookings, SD Location

| Treatment | Variety | Ratio | Rank | Location | Trial | Yield |
|---|---|---|---|---|---|---|
| TJ0300 | NK3030Bt | 0/100 | 6 | Brookings, SD | Liquid | 171.3 a |
| TJ1300 | NK3030Bt | 50/50 | 5 | Brookings, SD | Liquid | 180.7 ab |
| TJ1310 | NK3030Bt | 30/70 | 1 | Brookings, SD | Liquid | 185.8 b |
| TJ66/300 | NK3030Bt | 50/50 | 3 | Brookings, SD | Liquid | 181.6 ab |
| CV % | | | | | | 6.32 |
| LSD (0..20%) | | | | | | 11.40 |

TABLE 8

Liquid Drench Treatment on Corn Variety 3030Bt at Groton, SD Location

| Treatment | Variety | Ratio | Rank | Location | Trial | Yield |
|---|---|---|---|---|---|---|
| Control | NK3030Bt | 0/0 | 2 | Groton, SD | Liquid | 173.9 c |
| TJ1000 | NK3030Bt | 100/0 | 6 | Groton, SD | Liquid | 164.1 a |
| TJ0300 | NK3030Bt | 0/100 | 4 | Groton, SD | Liquid | 171.3 abc |
| TJ1300 | NK3030Bt | 50/50 | 3 | Groton, SD | Liquid | 171.5 abc |
| TJ1310 | NK3030Bt | 30/70 | 1 | Groton, SD | Liquid | 176.3 c |
| TJ66/300 | NK3030Bt | 50/50 | 5 | Groton, SD | Liquid | 164.4 ab |
| CV % | | | | | | 10.92 |
| LSD (0.20%) | | | | | | 8.42 |

WORKING EXAMPLE NO. 8

Materials and Methods: A field trial was conducted using the corn variety NK 3030Bt at a location in Groton, S.Dak. The purpose of the trial was to compare the compatibility and yield benefit of the biocontrol preparation TJ 1300 in combination with a dry granule micro-nutrient fertilizer vs. the micro-nutrient fertilizer alone vs. a control with no micro-nutrient fertilizer. The micro-nutrient fertilizer is sold commercially by the applicant under the trademark TJ Micromix™. Biocontrol treatments were prepared by adding 1×10⁶ CFU per seed. The control seed was Maxim (Maxim is a trademark of Syngenta Crop Protection) treated with the biocontrol treatments applied in addition to the Maxim. The seed was planted at a seeding rate of 25,000 seeds per acre in 30-inch rows in a randomized, replicated block. TJ Micromix™ was applied at a rate of 20 pounds per acre. Each entry was replicated four times. The pathogen levels were natural populations at each location. The entries were as follows:

Control: Maxim

TJ Micromix

TJ Micromix+TJ 1300—50/50 combination of *B. amyloliquifaciens* TJ1000 or 1BE and *T. virens* GL-3

Results: In this trial, as shown in Table 9, the Granular TJ Micromix produced a non-significant yield increase compared to the control. When the seed-applied biocontrol treatment TJ1300 was applied in combination with the TJ Micromix, the treatment resulted in a significant increase in yield.

Conclusion: The trial shows that TJ 1300 is compatible with micro-nutrient applications and the combination produces a significant yield response.

TABLE 9

Effect of TJ Micromix and TJ Micromix + TJ 1300 on Corn Variety NK 3030Bt

| Treatment | Variety | Rank | Location | Trial | Yield |
|---|---|---|---|---|---|
| Control | NK3030Bt | 3 | Groton, SD | Fertilizer | 157.0 a |
| TJ Micromix | NK3030Bt | 2 | Groton, SD | Fertilizer | 163.3 ab |
| TJ Micromix + TJ 1300 | NK3030Bt | 1 | Groton, SD | Fertilizer | 175.5 b |
| CV % | | | | | 9.04 |
| LSD (0.05%) | | | | | 5.64 |

WORKING EXAMPLE NO. 9

Materials and Methods: A field trial was conducted using the corn variety NK 3030Bt at a location in Groton, S.Dak. The purpose of the trial was to compare the compatibility and yield benefit of the biocontrol preparation TJ 1 300 in combination with a liquid chelate micro-nutrient fertilizer vs. the liquid chelate micro-nutrient fertilizer alone. The liquid chelate micro-nutrient fertilizer is sold commercially under the Trademark TJ Micromix™—Cornmix. Biocontrol treatments were prepared by adding 1×10⁶ CFU per seed. The control seed was Maxim (Maxim is a trademark of Syngenta Crop Protection) treated with the biocontrol treatments applied in addition to the Maxim. The seed was planted at a seeding rate of 25,000 seeds per acre in 30-inch rows in a randomized, replicated block. TJ Micromix™—Cornmix was applied at a rate of 1.5 quarts per acre. Each entry was replicated four times. The pathogen levels were natural populations at the location. The entries were as follows:

Control: Maxim+Liquid Chelate TJ Micromix

TJ Micro+TJ1000: Liquid Chelate TJ Micromix plus TJ 1000—*B. amyloliquifaciens* TJ1000 or 1BE TJ Micro+TJ0300: Liquid Chelate TJ Micromix plus TJ 0300—*T. virens* GL-3

TJ Micro+TJ1300: Liquid Chelate TJ Micromix+TJ 1300—50/50 combination of *B. amyloliquifaciens* TJ1000 or 1BE and *T. virens* GL-3

TJ Micro+TJ1310: Liquid Chelate TJ Micromix+TJ 1310—Coculture 30/70 combination of *B. amyloliquifaciens* TJ1000 or 1BE and *T. virens* GL-3

TJ Micro+TJ66/300: Liquid Chelate TJ Micromix+TJ 66/300—50/50 combination of *Bacillus lentimorbus* and *T. virens* GL-3

Results: As shown in Table 10, the biocontrol treatments TJ1000, 66/300, and 1300 combined with the liquid chelate TJ Micromix resulted in a significant increase in yield over the control of TJ Micromix alone. The other biocontrol entries showed numerical but non-significant increases in yield. The conclusion was that the biocontrol agents used in this study are compatible with liquid chelate micro-nutrient applications. This biocontrol/liquid chelate micro-nutrient fertilizer combination is a viable means to significantly increase the yield of corn.

TABLE 10

Effect of TJ Micromix Liquid Chelate and TJ Micromix Liquid Chelate + TJ 1300 on Yield of Corn Variety NK3030Bt

| Treatment | Variety | Ratio | Rank | Location | Trial | Yield |
|---|---|---|---|---|---|---|
| Control | NK3030Bt | 0/0 | 6 | Groton, SD | Liquid TJ Micromix | 161.0 a |
| TJ Micro + TJ 1000 | NK3030Bt | 100/0 | 3 | Groton, SD | Liquid TJ Micromix | 173.0 bc |
| TJ Micro + TJ 0300 | NK3030Bt | 0/100 | 5 | Groton, SD | Liquid TJ Micromix | 163.0 ab |
| TJ Micro + TJ 1300 | NK3030Bt | 50/50 | 1 | Groton, SD | Liquid TJ Micromix | 183.7 c |
| TJ Micro + TJ 1310 | NK3030Bt | 30/70 | 4 | Groton, SD | Liquid TJ Micromix | 172.0 ab |
| TJ Micro + TJ 66/300 | NK3030Bt | 50/50 | 2 | Groton, SD | Liquid TJ Micromix | 173.2 bc |
| CV % | | | | | | 11.2 |
| LSD (0.05%) | | | | | | 12.36 |

WORKING EXAMPLE NO. 10

Materials and Methods; A field trial was conducted using the sunflower variety Pioneer 63M80 NuSun at a location in Hazelton, N.Dak. The purpose of the trial was to compare the compatibility and yield benefit of the biocontrol preparation TJ1300 in combination with a dry granule micro-nutrient fertilizer vs. the micro-nutrient fertilizer alone vs. a control with no micro-nutrient fertilizer. Analyzing yield of sunflower is a function of seed yield in pounds per acre and the amount of oil in the seed which is expressed as a percentage. The micro-nutrient fertilizer is sold commercially under the Trademark TJ Micromix™. Biocontrol treatments were prepared by adding $1\times10^6$ CFU per seed. The control seed was Maxim (Maxim is a trademark of Syngenta Crop Protection) treated with the biocontrol treatments applied in addition to the Maxim. The seed was planted at a seeding rate of 22,000 seeds per acre in 30-inch rows in a randomized, replicated block. TJ Micromix™ was applied at a rate of 20 pounds per acre. Each entry was replicated four times. The pathogen levels were natural populations at the location. The entries were as follows:

Control: Maxim

TJ Micromix

TJ 1300—50/50 combination of *B. amyloliquifaciens* TJ1000 or 1BE and *T virens* GL-3

TJ Micromix+TJ 1300—50/50 combination of *B. amyloliquifaciens* TJ1000 or 1BE and *T. virens* GL-3

Results: As shown in Table 11, in this trial, the Granular TJ Micromix produced a significant yield increase and a significant oil percentage increase compared to the control. When the seed-applied biocontrol treatment TJ1300 was applied in combination with the TJ Micromix, the treatment resulted in a significant increase in yield as compared to the control but not significantly different from the TJ Micromix application alone. The yield of the TJ 1300+TJ Micromix was numerically higher in yield. The conclusion was that TJ 1300 is compatible with micro-nutrient applications and may be a viable tool to increase the yield of sunflower.

TABLE 11

Effect of TJ1300 Liquid Biological Treatment Plus Dry Granular TJ Micromix on Yield of Nu-sun Sunflower Variety 63M80

| Treatment | Rank | Location | Trial | Yield | Oil[001b] |
|---|---|---|---|---|---|
| Control | | Hazelton, ND | TJ Micro | 1709.7 a | 44.8 a |
| TJ Micromix | | Hazelton, ND | TJ Micro | 1857.3 bc | 47.2 b |
| TJ 1300 | | Hazelton, ND | TJ Micro | 1734.7 ab | 45.5 a |
| TJ 1300 + TJ Micromix | | Hazelton, ND | MM | 1864.7 bc | 44.9 a |
| CV % | | | | 7.48 | 4.67 |
| LSD (0.20) | | | | 132.8 | 1.5 |

WORKING EXAMPLE NO. 11

Materials and Methods: Field trials was conducted using the sunflower variety Pioneer 63M80 NuSun at 3 locations: Hazelton, N.Dak.; Kensal, N.Dak.; and Selby, S.Dak. The purpose of each trial was to compare the compatibility and yield benefit of the biocontrol preparation TJ1300 in combination with a liquid chelate micro-nutrient fertilizer vs. an untreated control. Analyzing yield of sunflower is a function of seed yield in pounds per acre and the amount of oil in the seed which is expressed as a percentage. The liquid chelate micro-nutrient fertilizer is sold commercially under the Trademark TJ Micromix™. Biocontrol treatments were prepared by adding $1\times10^8$ CFU per gram to a wettable powder (Mycotech, Inc). 25 grams of the wettable powder was then added to 1.5 quarts of liquid chelate TJ Micromix and the combination applied in the seed furrow at a rate of 1.5 quarts per acre. The control seed was Maxim (Maxim is a trademark of Syngenta Crop Protection) treated with the biocontrol treatments applied in addition to the Maxim. The seed was planted at a seeding rate of 22,000 seeds per acre in 30-inch rows in a randomized, replicated block. Each entry was replicated four times. The pathogen levels were natural populations at each location. The entries were as follows:

Control—no treatment

TJ 1300—50/50 combination of *B. amyloliquifaciens* GL-3 and *T. virens* GL-3

TJ1300+TJ Micromix—Liquid chelate TJ Micromix+50/50 combination of *B. amyloliquifaciens* and *T. virens*

Result: As shown in Table 12, TJ Micromix liquid and the combination of TJ Micromix plus TJ 1300 both gave sunflower a significant increase in yield. TJ 1300+TJ Micromix produced an additional numerical increase in yield over the TJ Micromix alone.

Conclusion: TJ 1300+TJ Micromix is a viable means of biocontrol delivery on sunflower and is a viable means of increasing the seed yield of sunflower.

TABLE 12

Effect of TJ1300 Biological Liquid Plus Liquid TJ Micromix Fertilizer on Yield of Nu-sun Sunflower Variety 63M80

| Treatment | Ratio | Location | Trial | Yield | Oil |
|---|---|---|---|---|---|
| Control | 0/0 | Hazelton, ND | Liquid TJ Micro | 1709.7 | 44.8 |
| TJ 1300 | 50/50 | Hazelton, ND | Liquid TJ Micro | 1765.0 | 45.5 |
| TJ1300 + TJ Micromix | 50/50 | Hazelton, ND | Liquid TJ Micro | 1992.3 | 45.9 |

TABLE 12-continued

Effect of TJ1300 Biological Liquid Plus Liquid TJ Micromix Fertilizer on Yield of Nu-sun Sunflower Variety 63M80

| Treatment | Ratio | Location | Trial | Yield | Oil |
|---|---|---|---|---|---|
| Control | 0/0 | Kensal, ND | Liquid TJ Micro | 2000.3 | N/a |
| TJ1300 | 50/50 | Kensal, ND | Liquid TJ Micro | 2159.0 | N/a |
| TJ1300 + TJ Micromix | 50/50 | Kensal, ND | Liquid TJ Micro | 2329.0 | N/a |
| Control | 0/0 | Selby, SD | Liquid TJ Micro | 2225.0 | 43.2 |
| TJ 1300 | 50/50 | Selby, SD | Liquid TJ Micro | 2324.0 | 44 |
| TJ1300 + TJ Micromix | 50/50 | Selby, SD | Liquid TJ Micro | 2228.5 | 44 |
| Control Average | | | | 1978.3 a | 44 a |
| TJ 1300 | | | | 2082.8 b | 44.75 a |
| TJ1300 + TJ Micromix | | | | 2173.3 b | 45.5 a |
| CV % | | | | 10.58 | 4.67 |
| LSD (0.05) | | | | 104.1 | NS |

WORKING EXAMPLE NO. 12

Materials and Methods: A field trial was conducted using the soybean variety Pioneer 91B52 a location near Groton, S.Dak. The purpose of the trial was to compare the compatibility and yield benefit of the biocontrol preparation TJ1300 in combination with a liquid chelate micro-nutrient fertilizer vs. the liquid chelate alone vs. an untreated control. Yield in bushels per acre was used as the measure of the treatment response. The liquid chelate micro-nutrient fertilizer is sold commercially under the Trademark TJ Micromix™. Biocontrol treatments were prepared by adding $1\times10^8$ CFU per gram to a wettable powder (Mycotech, Inc). Twenty-five grams of the wettable powder was then added to 10 gallons of water and applied in the seed Arrow at a rate of 10 gallons per acre to establish treatment TJ1300. Twenty-five grams of the wettable powder was added to 1.5 quarts of liquid chelate TJ Micromix and the combination added to water to form a 10 gallon solution and applied in the seed furrow at a rate of 10 gallons per acre. The seed was planted at a seeding rate of 175,000 seeds per acre in 30-inch rows in a randomized, replicated block. Each entry was replicated four times. The pathogen levels were natural populations at the location. The entries were as follows:

Control—no treatment

TJ 1300—50/50 combination of *B. amyloliquifaciens* TJ1000 or 1BE and *T. virens* GL-3

TJ1300+TJ Micromix—Liquid chelate TJ Micromix+50/50 combination of *B. amyloliquifaciens* TJ1000 or 1BE and *T. virens* GL-3

Result: As shown in Table 13, TJ Micromix liquid and the combination of TJ Micromix plus TJ 1300 both gave soybean a significant increase in yield. TJ 1300+TJ Micromix produced an additional numerical but non significant increase in yield over the TJ Micromix alone.

Conclusion: TJ 1300+TJ Micromix is a viable means of biocontrol deliver on soybean and is a viable means of increasing the yield of soybean.

TABLE 13

Effect of TJ1300 Liquid Biological Treatment Plus Liquid TJ Micromix Fertilizer on Yield of Soybean Variety 91B52

| Treatment | Ratio | Location | Trial | Yield |
|---|---|---|---|---|
| Control | 0/0 | Groton, SD | Liquid TJ Micromix | 54.2 a |
| TJ 1300 | 50/50 | Groton, SD | Liquid TJ Micromix | 60.8 b |
| TJ1300 + TJ Micromix | 50/50 | Groton, SD | Liquid TJ Micromix | 61.8 b |
| CV % | | | | 8.92 |
| LSD (0.05) | | | | 4.19 |

WORKING EXAMPLE NO. 13

Materials and Methods: A field trial was conducted using the soybean variety Pioneer 91B52 at a location near Groton, S.Dak. The purpose of the trial was to compare the compatibility and yield benefit of the biocontrol preparation TJ1300 in combination with a dry granule micro-nutrient fertilizer vs. the micro-nutrient fertilizer alone vs. a control with no micro-nutrient fertilizer. Soybean yield in bushels per acre was used to measure the treatment response. The micro-nutrient fertilizer is sold commercially under the Trademark TJ Micromix™. Biocontrol treatments were prepared by adding $1\times10^5$ CFU per seed. The seed was planted at a seeding rate of 175,000 seeds per acre in 30-inch rows in a randomized, replicated block. TJ Micromix™ was applied at a rate of 20 pounds per acre. Each entry was replicated four times. The pathogen levels were natural populations at each location. The entries were as follows:

Control: Maxim

TJ Micromix

TJ 1300—50/50 combination of *B. amyloliquifaciens* TJ1000 or 1BE and *T. virens* GL-3

TJ Micromix+TJ 1300—50/50 combination of *B. amyloliquifaciens* TJ1000 or 1BE and *T. virens* GL-3

Results: As shown in Table 14, in this trial, the Granular TJ Micromix produced a significant yield increase compared to the control. When the seed-applied biocontrol treatment TJ1300 was applied in combination with the TJ Micromix, the treatment resulted in a significant increase in yield as compared to the control but not significantly different from the TJ Micromix application alone. The yield of the TJ 1300+TJ Micromix was numerically higher.

Conclusion: TJ 1300 is compatible with micro-nutrient applications and is a viable tool to increase the yield of soybean.

TABLE 14

Effect of TJ1300 Biological Seed Treatment Plus Dry Granule TJ Micromix Fertilizer on Yield of Soybean Variety 91B52

| Treatment | Ratio | Location | Trial | Yield |
|---|---|---|---|---|
| Control | 0/0 | Groton, SD | TJ Micro | 54.2 a |
| TJ Micromix Granule | 0/0 | Groton, SD | TJ Micro | 61.6 b |
| TJ 1300 | 50/50 | Groton, SD | TJ Micro | 62.5 b |
| TJ 1300 + TJ Micromix | 50/50 | Groton, SD | TJ Micro | 63.3 b |
| CV % | | | | 8.92 |
| LSD (0.05) | | | | 4.19 |

WORKING EXAMPLE NO. 14

Materials and Methods: A field trial was conducted using Russ Spring wheat at a location near Kensal, N.Dak. The purpose of the trial was to test biocontrol TJ 1300 on spring wheat against an untreated control. The biocontrol TJ 1300 was applied to the seed so as to achieve an application rate of $2.5 \times 10^9$ CFU per acre. The plot was planted in a randomized, replicated block design with each entry replicated three times.

Result: As shown in Table 15, the entry TJ 1300 produced a non-significant yield increase. The conclusion was that TJ 1300 may be of value as a seed treatment on wheat.

TABLE 15

Effect of TJ1300 Biological Seed Treatment Plus Fertilizer on Russ Spring Wheat

| Treatment | Ratio | Location | Trial | Yield |
|---|---|---|---|---|
| Control | 0/0 | Kensal, ND | MM | 43.8 |
| 1300 | 50/50 | Kensal, ND | MM | 44.0 |
| CV % | | | | 7.52 |
| LSD (0.05) | | | | NS |

WORKING EXAMPLE NO. 15

Materials and Methods: A field trial was conducted to compare the biocontrol treatment TJ 1300 to a non-treated control on field peas. The seed was treated with the biocontrol agent to achieve an application of $2.5 \times 10^9$ CFU per acre. Yield response was measured as pounds per acre.

Results: As shown in Table 16, the entry TJ 1300 produced a non-significant yield increase in field peas. The conclusion was that TJ 1300 may be an effective tool to increase the yield of field peas.

TABLE 16

Effect of TJ1300 Biological Seed Treatment on Yield of Integra Field Pea

| Treatment | Ratio | Rep | Location | Trial | Yield | Test wieght |
|---|---|---|---|---|---|---|
| Control | 0/0 | Ave of 3 | Carrington, ND | Pea | 3590.0 | 62.9 |
| 1300 | 50/50 | Ave of 3 | Carrington, ND | Pea | 3613.0 | 63.5 |
| CV % | | | | | 7 | 0.5 |
| LSD (0.05) | | | | | ns | ns |

Many variations of the invention will occur to those skilled in the art. Some variations include noncompetitive culturing of the biocontrol organisms. Other variations call for competitive culturing. All such variations are intended to be within the scope and spirit of the invention.

What is claimed is:

1. An agricultural inoculum suitable for inoculating plant seeds, said inoculum comprising:
    a fungal antagonist selected from the group consisting of *Trichoderma virens* isolate (ATCC 58678) and mutants thereof;
    a bacterial antagonist selected from the group consisting of *Bacillus subtilis* var. *amyloliquifaciens* strain (ATCC BAA-390) and mutants thereof; and
    a suitable carrier that is non-phytotoxic, non-bacteriostatic, and non-bacteriocidal.

2. A method of protecting a seed or a plant from disease caused by a plant pathogenic fungus comprising:
    inoculating seeds from said plant with a composition comprising the agricultural antagonist of claim 1;
    wherein said combination suppresses growth of plant pathogenic fungi.

3. The method of claim 2 wherein the combination suppresses growth of the plant pathogen fungi Fusarium, Phythium, Phytophthora and Penicillium.

4. A method for protecting plants in a growing medium from damping off and root rot fungal plant disease comprising:
    placing in the growing medium in the immediate vicinity of the plant to be protected an effective quantity of the agricultural inoculum of claim 1.

5. A method for protecting plants from fungal plant disease comprising:
    adding the composition of claim 1 in an effective quantity to a substrate selected from the group consisting of pelletized calcium sulfate or pelletized lime; and
    placing the pellet in the immediate vicinity of the plant to be protected.

6. The method of claim 5 further comprising:
    adding another plant growth nutrient to the pellet.

7. A method for protecting a plant from fungal plant disease comprising:
    adding the agricultural inoculum of claim 1 in an effective quantity to a liquid solution; and
    applying the liquid solution in the immediate vicinity of the plant.

8. The method of claim 7 further comprising:
    adding an additive to the liquid, said additive being at least one substance selected from the group consisting of
    a plant nutrient,
    a plant micro-nutrient, and
    a chemical fungicide.

9. A method for biologically controlling a plant disease caused by a plant-colonizing fungus, the method comprising:
    inoculating a seed of the plant with an effective amount of a microbial inoculant comprising a combination having all of the identifying characteristics of the agricultural inoculum of claim 1, said inoculation resulting in the control of said plant disease.

10. The method of claim 9 wherein said inoculation results in the control of more than one plant disease.

11. A process comprising:
    making the agricultural inoculum of claim 1; and
    applying said agricultural inoculum to a seed;
    wherein said agricultural inoculum ranges in composition from 1 to 99 percent *Trichoderma virens* (ATCC 58678) by culture volume and from 99 to 1 percent *Bacillus amyloliquefaciens* (ATCC BAA-390) by culture volume.

12. A composition of matter comprising:
    a plant seed inoculated with the agricultural inoculum of claim 1;
    wherein said combination increases the yield of the plant.

13. A method for increasing the yield of a plant, the method comprising:
    coating a seed of the plant with an effective amount of the agricultural inoculum of claim 1; and
    culturing the plant.

14. A composition of matter comprising:
    a plant seed inoculated with a combination comprising a fungal antagonist selected from the group consisting of *Trichoderma virens* (ATCC 58678) and mutants thereof and a bacterial antagonist selected from the group consisting of *Bacillus amyloliquefaciens* (ATCC BAA-390) and mutants thereof;

wherein said combination suppresses growth of plant pathogenic fungi.

15. A plant inoculated with a combination comprising:
a fungal antagonist selected from the group consisting of Trichoderma virens (ATCC 58678) and mutants thereof; and
a bacterial antagonist selected from the group consisting of Bacillus amyloliquefaciens (ATCC BAA-390) and mutants thereof;
wherein the combination suppresses growth of plant pathogenic fungi and the plant is selected from the group consisting of
corn,
sunflower,
soybean,
field pea, and
wheat.

16. A method of protecting a plant from disease caused by a plant pathogenic fungus comprising:
inoculating seeds from said plant with a combination comprising a fungal antagonist selected from the group consisting of Trichoderma virens (ATCC 58678) and mutants thereof and a bacterial antagonist selected from the group consisting of Bacillus amyloliquefaciens (ATCC BAA-390) and mutants thereof;
wherein said combination suppresses growth of plant pathogenic fungi.

17. A method for biologically controlling or inhibiting stalk rot or root rot comprising:
coating seeds with an effective amount of a composition comprising Trichoderma virens (ATCC 58678) and Bacillus amyloliquefaciens (ATCC BAA-390).

18. A process for making a composition comprising:
introducing an essentially pure culture of Bacillus amyloliquefaciens (ATCC BAA-390) to a growth medium about eight hours after an essentially pure culture of Trichoderma virens (ATCC 58678) is introduced to the growth medium; and
growing the culture as a competitive culture.

19. A process comprising making a composition comprising:
combining an essentially pure culture of Trichoderma virens (ATCC 58678) with an essentially pure culture of Bacillus amyloliquefaciens (ATCC BAA-390) in a 50:50 mixture; and
applying said composition to a seed at a rate of at least 100,000 spores per seed.

20. A composition of matter made by combining:
a fungal antagonist selected from the group consisting of Trichoderma virens isolate (ATCC 58678) and mutants thereof;
a bacterial antagonist selected from the group consisting of Bacillus subtilis var. amyloliquifaciens strain (ATCC BAA-390) and mutants thereof; and
a suitable carrier that is non-phytotoxic, non-bacteriostatic, and non-bacteriocidal.

21. A method comprising:
combining a spore-forming fungal strain and a spore-forming bacterial strain to produce a product comprising the composition of matter of claim 20; and
applying the product to a plant;
whereby application of the product produces yield enhancement in the plant.

22. An antagonist for controlling plant pathogens made by combining effective amounts of:
a fungal antagonist selected from the group consisting of Trichoderma virens isolate (ATCC 58678) and mutants thereof;
a bacterial antagonist selected from the group consisting of Bacillus subtilis var. amyloliquifaciens strain (ATCC BAA-390) and mutants thereof; and
a suitable carrier that is non-phytotoxic, non-bacteriostatic, and non-bacteriocidal.

23. An antagonist made by further combining with the antagonist of claim 22 an effective amount of another bacterial strain.

24. A method for culturing a plant comprising:
applying the antagonist of claim 22 to a seed or to the seedbed of the plant;
planting the seed in the seedbed;
growing the plant to yield a crop; and
harvesting the crop;
wherein said applying step increases the yield of the crop.

25. The method of claim 24 wherein the antagonist is applied to the seed or to the seedbed of a plant selected from the group consisting of
a monocot, and
a dicot.

26. The method of claim 24 wherein the antagonist is applied to the seed or to the seedbed of a plant selected from the group consisting of
a legume plant, and
a non-legume plant.

27. The method of claim 24 wherein the antagonist is applied to the seed or to the seedbed of a plant selected from the group consisting of
corn,
sunflower,
soybean,
field pea, and
wheat.

28. A method comprising:
applying a Trichoderma spp. microorganism and a Bacillus spp. microorganism to a wettable powder to produce a combination comprising the antagonist of claim 22; and
applying the combination to a seed;
whereby application of the combination produces a positive yield response in a plant growing from the seed.

29. A process comprising:
making a composition by combining an essentially pure culture of Trichoderma virens (ATCC 58678) with an essentially pure culture of Bacillus amyloliquefaciens (ATCC BAA-390) in a mixture; and
applying said composition to a seed; wherein said mixture ranges in composition from 10 to 90 percent Trichoderma virens (ATCC 58678) by culture volume and from 90 to 10 percent Bacillus amyloliquefaciens (ATCC BAA-390) by culture volume.

30. A process comprising:
making a composition by combining an essentially pure culture of Trichoderma virens (ATCC 58678) with a plurality of essentially pure cultures of bacteria in a mixture; and
applying said composition to a seed; wherein said mixture ranges in composition from 10 to 90 percent Trichoderma virens (ATCC 58678) by culture volume.

* * * * *